United States Patent [19]

Mingozzi

[11] Patent Number: 5,057,113

[45] Date of Patent: Oct. 15, 1991

[54] DEVICE FOR TENSIONING TRACTION WIRES IN ORTHOPEDIC SURGERY

[75] Inventor: Franco Mingozzi, Lippo Di Calderara Di Reno, Italy

[73] Assignee: Citieffe S.r.l., Lippo Di Calderara Di Reno, Italy

[21] Appl. No.: 502,884

[22] Filed: Apr. 2, 1990

[30] Foreign Application Priority Data

Apr. 3, 1989 [IT] Italy .................... 3410 A/89

[51] Int. Cl.$^5$ .................................. A61B 17/56
[52] U.S. Cl. ............................. 606/103; 606/56
[58] Field of Search ....................... 606/53–57, 606/59, 103; 81/315, 9.41, 9.42, 9.43

[56] References Cited

U.S. PATENT DOCUMENTS

| | | | |
|---|---|---|---|
| 2,049,361 | 7/1936 | Ericsson | 606/103 |
| 4,338,927 | 7/1982 | Volkov et al. | 606/55 X |
| 4,557,164 | 12/1985 | Krampe | 81/9.41 |
| 4,768,524 | 9/1988 | Hardy | 606/54 |
| 4,923,458 | 5/1990 | Fischer | 606/57 X |
| 4,936,843 | 6/1990 | Sohngen | 606/57 X |
| 4,966,600 | 10/1990 | Songer et al. | 606/103 X |

FOREIGN PATENT DOCUMENTS 6125 10/1987 World Int. Prop. O. ............ 606/59

Primary Examiner—Robert A. Hafer
Assistant Examiner—Kevin G. Rooney
Attorney, Agent, or Firm—Guido Modiano; Albert Josif

[57] ABSTRACT

The device for tensioning traction wires has a hollow body to which a pair of actuation levers is pivoted. A movable head is guided frontally in the hollow body and a slider is slidably mounted inside the hollow body and is adapted to be traversed by a traction wire. A tension element is supported by the slider and provided with clamps for locking the traction wire. A lever system transmits to the slider the compression force exerted on the actuation levers, while an anchoring element rigidly associated with the hollow body is fitted on the slider, to which the lever system is pivoted. A movable locking element is adapted to keep constant the tension exerted by means of the actuation levers.

11 Claims, 3 Drawing Sheets

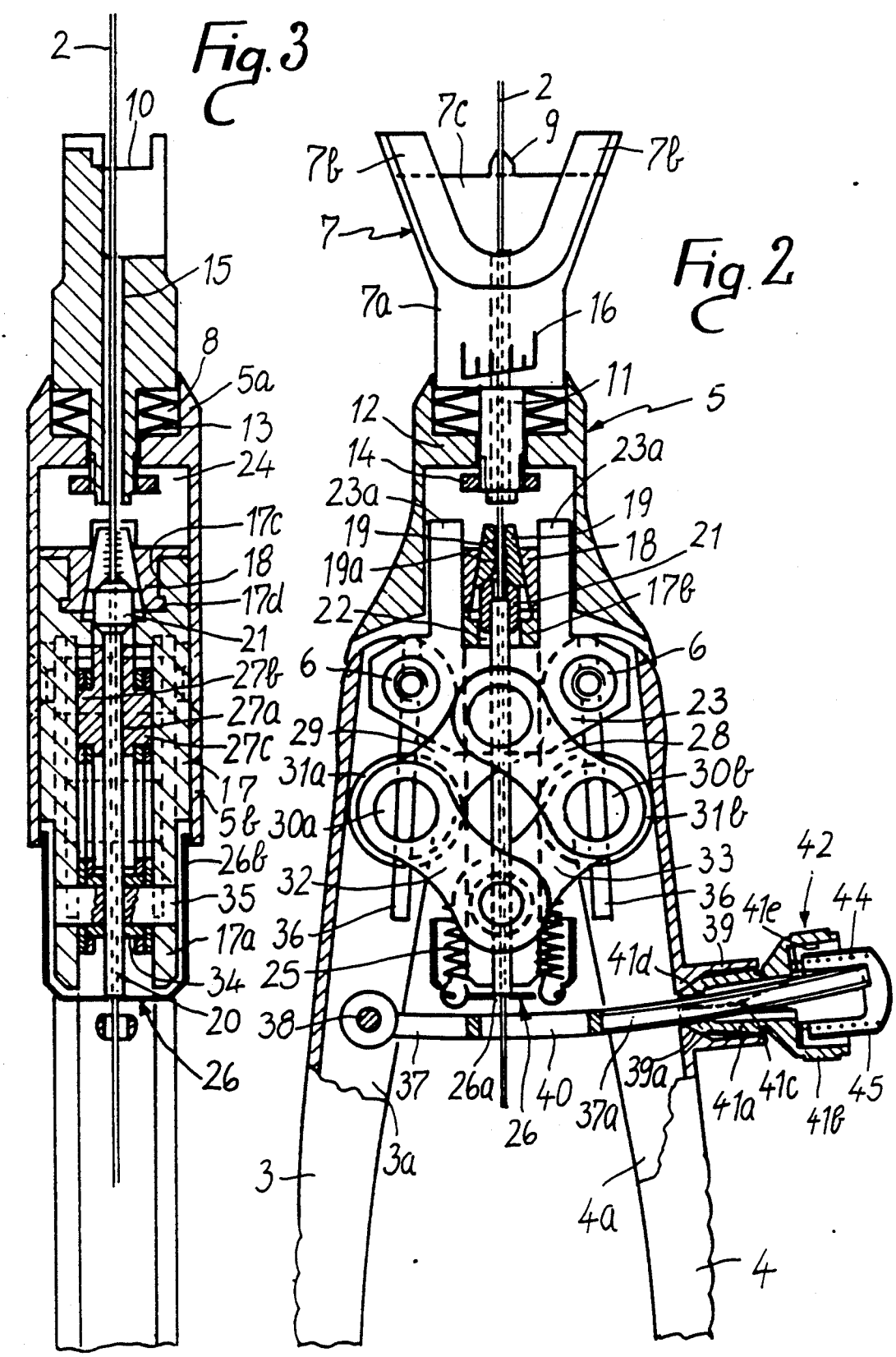

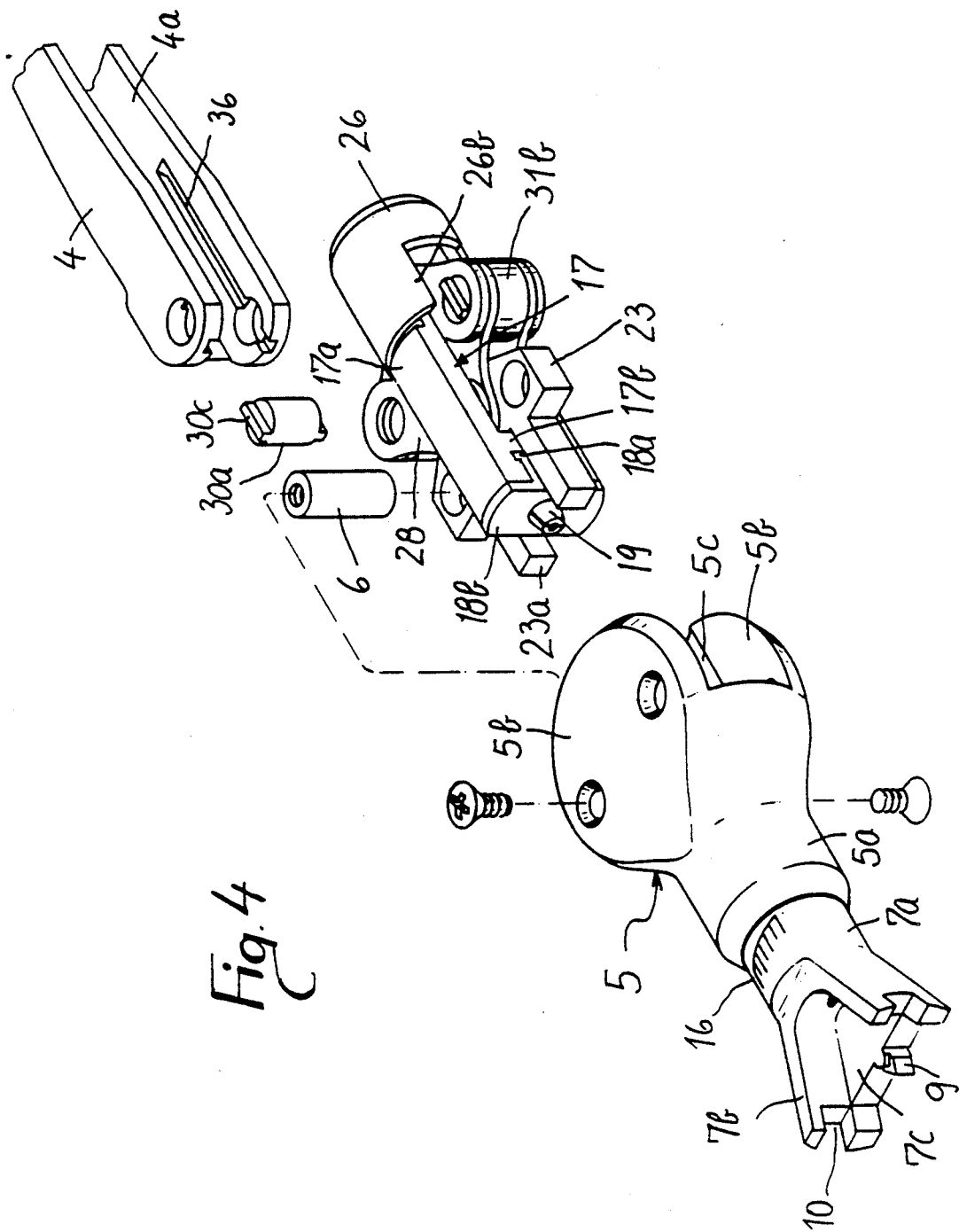

DEVICE FOR TENSIONING TRACTION WIRES IN ORTHOPEDIC SURGERY

BACKGROUND OF THE INVENTION

The present invention relates to a device for tensioning traction wires in orthopedic surgery, and in particular to a forceps-like for tensioning wires of the type known as "Kirschner's wires", during anchoring to external fixing devices.

As known, the method of direct traction on the skeleton is in widespread use for the therapy of bone fractures and other orthopedic treatments. Trans-skeletal wires, kept under tension by stirrup means and the like, according to Kirschner's improvement, are commonly used for this purpose.

The traction force is usually adjusted by means of suitable screw means or graduated weights and the like, and is often measured by means of conventional dynamometers.

The use of circular external fixing devices, substantially constituted by rings on which the traction wires are guided, has furthermore become widespread for some applications. During the fitting of said external fixing devices it is necessary to exert an adjustable, repeatable and verifiable traction on the wires.

SUMMARY OF THE INVENTION

Accordingly, the aim of the present invention is to solve the above problem by providing a device which allows to exert a constant and adjustable traction on Kirschner's wires and to provide a direct reading of the exerted traction.

Within the scope of this aim, a further object of the present invention is to provide a device for tensioning traction wires which is simple in concept, safe and reliable in operation and easy to use, as well as being versatile in use in the specified field.

This aim and this object as well as other objects which will become apparent hereinafter, are achieved, according to the invention, by the present device for tensioning traction wires in orthopedic surgery, which is characterized in that it comprises a hollow body, at least one pair of actuation levers pivoted on said body, a movable head frontally guided in said hollow body, a slider slidably mounted inside said hollow body and adapted to be traversed by at least one traction wire, at least one traction element supported by said slider and being provided with clamps for locking said traction wire, an anchoring element rigidly associated with said hollow body and being provided with guide means for guiding said slider, lever means pivoted to said anchoring element and adapted to transmit to said slider compression force exerted on said actuation levers, and locking means whereby to keep constant the tension exerted by means of said actuation levers.

BRIEF DESCRIPTION OF THE DRAWINGS

Further details of the invention will become apparent from the following detailed description of a preferred embodiment of the device for tensioning traction wires, illustrated only by way of non-limitative example in the accompanying drawings, wherein:

FIG. 2 is an enlarged-scale view of the forceps-like device of FIG. 1, showing the device in a traction cable tensioning position;

FIG. 3 is a median longitudinal sectional view thereof;

FIG. 4 is an exploded fragmentary perspective view of the traction cable tensioning device, showing the hollow body and the elements rigidly associated therewith.

DESCRIPTION OF THE PREFERRED EMBODIMENTS

Figure 1:
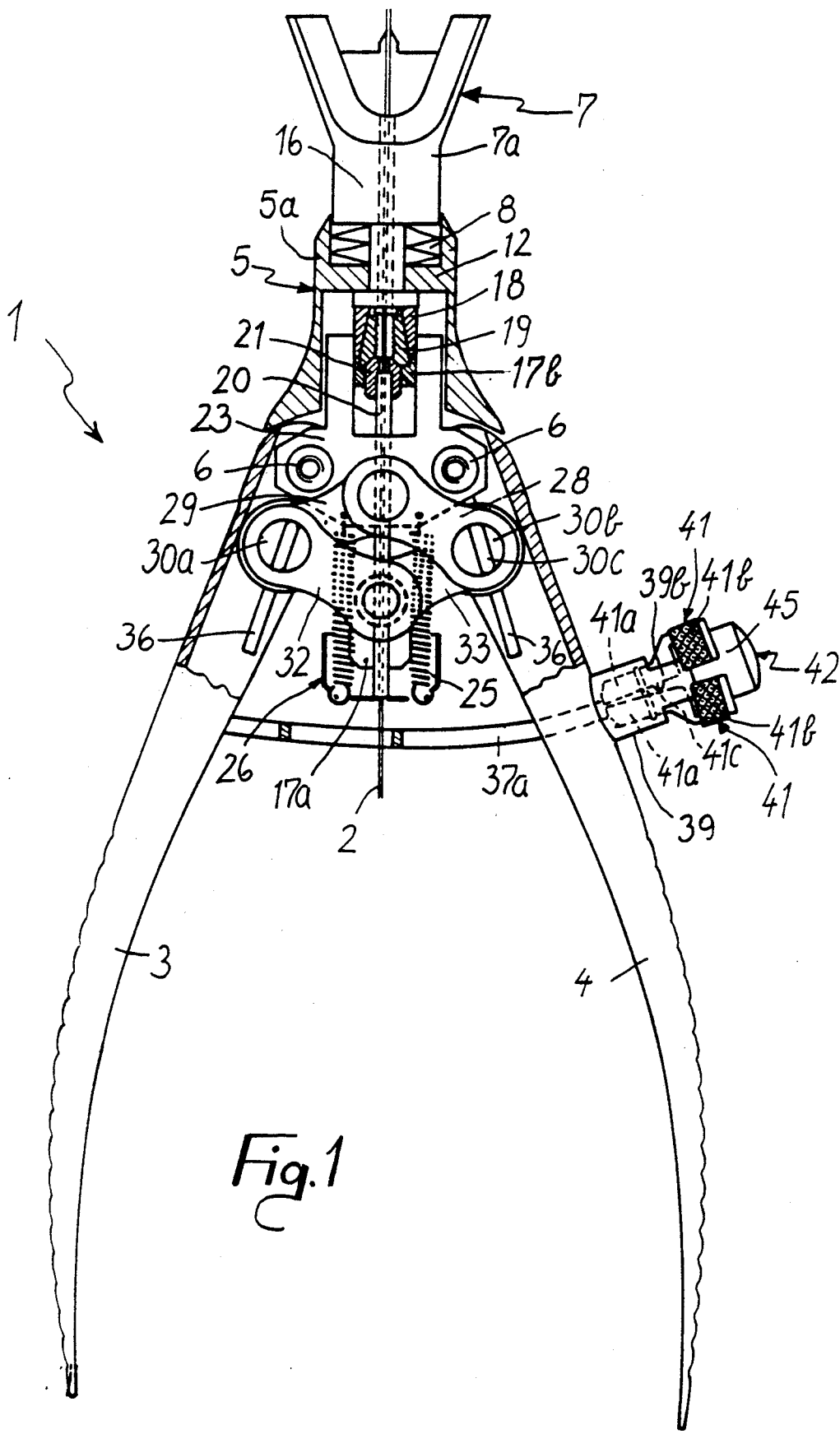
FIG. 1 is a partially sectional plan view of the forceps-like device for tensioning traction wires according to the invention, in a position of insertion of the wire to be tensioned.

With particular reference to the above-described drawing figures, the forceps-like device for tensioning traction wires 2, such as Kirschner's wires, is generally indicated by the reference numeral 1. The wire tensioning device is substantially constituted by a pair of levers 3, 4 each having an end pivoted simmetrically to a hollow body 5.

The body 5 is bell-shaped and has a front cylindrical portion 5a and a widened rear portion defined between a pair of walls 5b. The levers 3, 4 are articulated between the walls 5b and are rotatable on respective pivots 6 which may be internally threaded for coupling to related screws. The levers 3, 4 each have a C-shaped cross section so as to define, between respective walls 3a, 4a, a channel-like configuration which is open toward the inside of the forceps-like device and which decreases in depth as it extends away from the end of the lever articulated to the pivot 6.

A movable head 7 protrudes frontally from the body 5 and is intended to engage the conventional ring-shaped fixing device (not illustrated for clarification purposes) of the wire 2. The movable head 7 defines a cylindrical portion 7a which is slidably mounted in a seat 8 defined axially in the front portion 5a of the body 5. A fork-like element extends from the cylindrical portion 7a and has branches 7b, which are divaricated and interconnected by a wing 7c from which a point 9 protrudes longitudinally. The branches 7b are each frontally provided with a respective recess 10, by means of which said head 7 is adapted to engage with the ring of a fixing device.

On the opposite side with respect to the branches 7b, the head defines a stem 11 which is guided in a central hole of a diaphragm or wall 12 which rearwardly closes the seat 8 of the body 5. The head 7 is actuated by elastic biasing means advantageously constituted by a plurality of cup springs 13 which act between the wall 12 and the bottom of the portion 7a of said head. The head is retained in the seat 8 by a nut 14 which is screwed to the end of the stem 11.

The head 7 is axially rotatable and is axially provided with a hole 15 through which a traction wire 2 can be passed. The cylindrical portion 7a of the head furthermore has a graduated scale 16 for reading the exerted traction.

A H-shaped slider 17, constituted by a pair of parallel and facing strips or slider members 17a joined by a transverse bridge 17b, is arranged so as to be longitudinally slidable between the walls 5b of the rear portion of the body 5. Said strips 17a define, in front of the bridge 17b, a seat 17c for the coupling of a traction element 18.

The traction element 18 is constituted by a bush which is provided with flanges 18a, 18b (see FIG. 4) and is flattened on two opposite lateral faces. The bush 18 is adapted to engage in a bayonet-like fashion in the seat 17c by virtue of the engagement of the flange 18a in a groove 17d of the seat 17c. In engagement position, the flange 18b rests on the front end of the strips 17a. The bush is axially provided with a conical seat in which a pair of clamps 19 for locking the traction wire 2 is accommodated. The clamps 19 externally define a conical shape, which matches the shape of the conical seat and they are internally provided with a set of teeth 19a.

A tube 20 for guiding the traction wire 2 extends between the strips 17a. The front end of the tube 20 is inserted in an end bush 21 which allows to guide said tube at a central hole 22 defined in the bridge 17b of the slider.

The slider 17 slides on an anchoring element 23 constituted by a stirrup-like element which has a flattened shape on the plane of actuation of the levers 3, 4 and is arranged between the strips 17a of the slider. In particular, the anchoring element 23 has a pair of arms 23a arranged astride the bridge 17b and accommodated in a seat 24 defined inside the body 5, behind the wall 12. The traction element 18 is guided between the arms 23a and its flattened faces are in sliding contact with the inner faces of said arms. The ends of a pair of helical springs 25 which retain a rear cup-shaped cover 26 are fixed to the anchoring element 23. Said lid 26 is adapted to act as an abutment for the end of the guiding tube 20 and has a hole 26a for the exit of the wire 2 inserted through the tube 20. In order to keep the hole 26a aligned with the tube 20, the edge of the corresponding end of said tube is expediently tapered so as to be caused to enter the hole 26a. The cove 26 has two extensions 26b (FIG. 3) with which it is guided between the walls 5b of the body 5. Cylindrical concave portions 5c (FIG. 4) are defined in the inner faces of the two walls 5b to guide the extensions 26b. The anchoring element 23 is axially traversed by a hole 27a in which the tube 20 is slidably guided, and has, on opposite sides, two raised portions 27b, 27c which constitute the articulation pivot of an extension lever system which is adapted to transmit the effort exerted on said levers 3, 4 to the slider 17.

The extension lever system comprises a system with a double articulated parallelogram; each parallelogram comprises a first pair of pivotally interconnected connecting rods 28, 29 which are symmetrically pivoted at one end on the pivot 27b, 27c and at the other end on respective pivots 30a, 30b inserted in respective rollers 31a, 31b. The rollers 31a, 31b rest on the inner walls of the levers 3, 4 and act as spacers between the connecting rods of one quadrilateral and those of the other one. Two further pairs of pivotally interconnected connecting rods 32, 33 are pivoted on the pivots 30a, 30b and are in turn pivoted on a bush 34 (FIG. 3) which is mounted on a further pivot 35 defined between the strips 17a of the slider 17. The bush 34 and the pivot 35 are diametrically perforated for permitting the insertion of the tube 20, which can thus rest on the cover 26.

To conclude, the two diagonally opposite vertices of the superimposed parallelograms formed by the connecting rods 28, 29 and 32, 33 are articulated on the pivot 27b, 27c and respectively on the bush 34 and pivot 35, and the other two vertices are articulated on the pivots 30a, 30b. Said pivots 30a, 30b have, at their ends, respective diametrical teeth 30c (FIG. 1) by means of which they are guided along grooves 36 defined along the walls 3a, 4a of the levers 3, 4.

The forceps-like device finally has a movable locking element adapted to maintain the compression applied on the levers 3, 4 even when the force on said levers ceases.

The locking element (FIGS. 1 and 2) comprises a curved stem 37 having and end which is pivotally connected to a pin 38 journalled to the lever 3 and a threaded portion 37a, which traverses the lever 4 through a sleeve 39 laterally rigidly associated with the lever 4. The stem 37 centrally defines a slot 40 for the passage of the traction wire 2.

Two half-bodies 41 of a knob 42 are supported in the sleeve 39 and have two tubular portions 41a which expand into two widened portions 41b which are also tubular and are externally knurled; the threaded portion 37a of the stem 37 is inserted between said widened portions. The half-bodies 41 are mutually pivotally connected to an axis 41c which is perpendicular to the stem 37 and are kept joined by an elastic ring 43 which is fitted in an outer annular groove. The ends of the tubular portions 41a which are inserted into the sleeve 39 have opposite sets of teeth 41d which are adapted to couple to the threaded portion 37a of the stem 37. The two widened portions 41b define a seat 41e for a return spring 44 which has the function of keeping the sets of teeth 41d coupled to the portion 37a of the stem 37. The locking of the sets of teeth 41d on the portion 37a is facilitated by a conical shaped configuration 39a arranged inside the sleeve 39.

The spring 44 is kept compressed by an internally threaded plug 45 which is screwed onto a pair of expansions 39b of the sleeve 39 which are threaded on their outer surface.

The operation of the above-described device substantially provides the insertion of the traction wire 2 inside the forceps-like device. The wire 2 is inserted in the axial hole 15 of the movable head 7 and is passed through the clamps 19a, 19b of the tension element 18 and the guiding tube 20, until it exits from the bottom of the cover 26. During the insertion step, the wire causes the partial widening of the clamps 19a, 19b which are moved to close, by means of the tube 20, by the elastic thrust exerted by the springs 25.

The other end of the traction wire 2 is coupled to the external fixing device by means of suitable means such as screw means. The movable head 7 is placed on the fixing device, moving the branches 7b tangentially into contact on the ring of said fixing device.

An appropriate manual compression is then exerted on the levers 3, 4 of the forceps-like device. The force exerted by the operator on the levers 3, 4 is transmitted to the slider 17 by means of the lever system formed by the connecting rods 28, 29 and 32, 33; the double parallelogram formed by said connecting rods in fact has a fixed axis formed by the pivots 27b, 27c of the anchoring element 23, so that the approach of the pivots 30a, 30b caused by the levers 3, 4 causes the spacing of the pivot 35 coupled to the slider 17.

The slider 17 slides along the traction axis, actuating the traction element 18 so as to lock the clamps 19a, 19b on the wire 2, as shown in FIG. 2, and so as to simultaneously exert a traction force with a tension which is proportional to the closure of the forceps-like device. The traction of the wire 2 furthermore causes the axial movement of the movable head 7 in contrast with the cup springs 13.

It is therefore possible to read the value of the traction exerted on the wire on the graduated scale 16 provided on the movable head 7 by taking as reference line the edge of the portion 5a. Said traction force can vary appropriately within a wide range according to requirements.

The knob-like locking element 42 allows to keep constant the tension exerted by means of the actuation levers until the wire is fixed. By actuating the levers 3,4 the portion 37a of the stem 37 in fact slides inside the knob and is locked by the set of teeth 41d of the tubular portions 41a by virtue of the thrust exerted by the spring 44 and by virtue of the conical portion 39a of the coupling with the sleeve 39.

In order to open the forceps-like device it is necessary to act on the knurled portions 41b of the knob 42 so as to open the set of teeth 41d and release the stem 37.

To conclude, the described forceps-like device allows to exert on Kirschner's wire a traction which can be modulated, is constant, repeatable and verifiable by means of a direct reading system. The fact should furthermore be noted that the actuation of the forceps-like device requires a very short manual procedure and minimal effort on the part of the operator.

In the practical embodiment of the invention, the materials employed, as well as the shape and dimensions, may be any according to the requirements.

I claim:

1. Device for tensioning traction wires during anchoring to external fixing devices in orthopedic surgery, comprising a hollow body to which a pair of actuation levers is pivoted, a movable head frontally guided in said hollow body, a slider slidably mounted inside said hollow body and adapted to be traversed by a traction wire, a traction element supported by said slider and provided with clamps for locking said traction wire, an anchoring element rigidly associated with said hollow body and provided with guiding means for said slider, lever means pivoted to said anchoring element and adapted to transmit to said slider compression force exerted on said actuation levers, and a movable locking element adapted to keep constant the tension exerted by means of said actuation levers.

2. Device according to claim 1, wherein said slider is defined by a pair of flanking strips which are guided between facing walls of said hollow body and are joined by a transverse wing which frontally defines the shaped bottom of a seat for the bayonet-like coupling of said traction element, an articulation pivot of said lever system being defined between said strips.

3. Device according to claim 1, wherein said traction element is constituted by a bush which is axially provided with a conical seat in which said clamps for locking the traction wire are accommodated.

4. Device according to claim 1, wherein said clamps externally have a conical shape and internally have a set of teeth for locking the traction wire.

5. Device according to claim 1, wherein a tube for guiding the traction wire is arranged longitudinally to said slider, engages said traction element at the front end and abuts, at the rear end, with a cover retained by means of spring means by said anchoring element.

6. Device according to claim 1, wherein said anchoring element is constituted by a stirrup-like element which has a flattened shape on the plane of actuation of said levers and inserts astride said slider so as to act as guide for said traction element.

7. Device according to claim 1, wherein said extension lever system is constituted by at least one articulated parallelogram formed by a first pair of connecting rods which are symmetrically pivoted, at one end, on an axis which is transverse to said anchoring element and by a second pair of connecting rods which are symmetrically pivoted, at one end, on an axis which is transverse to said slider, whereas at the opposite end said first and second pairs of connecting rods are pivoted on respective pivots which are respectively guided on said actuation levers.

8. Device according to claim 7, wherein said pivots have, at their ends, respective diametrical teeth by means of which they are guided along grooves provided along the edges of said actuation levers.

9. Device according to claim 1, wherein said movable head has a cylindrical portion which is slidably mounted, against the biasing action of spring means, in a seat which is defined axially with respect to said hollow body, a fork-like element extending from said cylindrical portion, said fork having divaricated arms which are frontally provided with respective recesses by means of which said head is adapted to engage on said fixing means.

10. Device according to claim 9, wherein said cylindrical portion of the movable head has a graduated scale for reading the exerted traction.

11. Device according to claim 1, wherein said movable locking element comprises a stem which is pivoted to an actuation lever and traverses, with a threaded portion, the opposite lever at a sleeve in which the half-bodies of a knob are inserted, said half-bodies being mounted so as to be oscillable about a central axis and internally having a set of teeth adapted to couple to said threaded portion of the stem, whereas at the opposite end they define the seat for a return spring which has the function of keeping the knob coupled to said stem, said spring being kept compressed by a plug screwed on expansions of said sleeve.

* * * * *